(12) United States Patent
Graus et al.

(10) Patent No.: US 6,632,459 B2
(45) Date of Patent: Oct. 14, 2003

(54) CHLOROGENIC ACID AND AN ANALOG THEREOF FOR IMMUNE SYSTEM STIMULATION

(75) Inventors: Yvo Maria Franciscus Graus, Ede (NL); Hobbe Friso Smit, Utrecht (NL); Albertus Dominicus Marcellinus Erasmus Osterhaus, Bunnik (NL); Robert Johan Joseph Hageman, Waddinxveen (NL)

(73) Assignee: Nutricia N.V., Zoetermeer (NL)

( * ) Notice: Subject to any disclaimer, the term of this patent is extended or adjusted under 35 U.S.C. 154(b) by 0 days.

(21) Appl. No.: 09/734,389

(22) Filed: Dec. 11, 2000

(65) Prior Publication Data

US 2002/0110606 A1 Aug. 15, 2002

(51) Int. Cl.[7] ............ A61K 35/78; A61K 31/235; A61K 33/32; A61K 33/34; A61K 33/04

(52) U.S. Cl. ............ 424/728; 424/725; 424/729; 424/737; 424/641; 424/702; 424/630; 424/769; 514/532; 514/533; 514/458; 514/706; 514/885

(58) Field of Search ............ 424/725, 728, 424/729, 769, 737, 641, 630, 702; 514/532, 533, 458, 706, 885

(56) References Cited

U.S. PATENT DOCUMENTS

| | | | |
|---|---|---|---|
| 2,073,616 A | | 3/1937 | Acree et al. |
| 4,454,286 A | | 6/1984 | Daniels et al. |
| 4,950,751 A | | 8/1990 | DeWitt |
| 5,080,906 A | * | 1/1992 | Carenzi et al. |
| 5,096,708 A | | 3/1992 | Gohla et al. |
| 5,788,971 A | | 8/1998 | Togasaki |
| 5,972,993 A | * | 10/1999 | Ptchelintsev |
| 6,331,565 B1 | * | 12/2001 | Dong et al. |

FOREIGN PATENT DOCUMENTS

| | | |
|---|---|---|
| EP | 0 606 080 | 7/1994 |
| EP | 0 906 761 | 4/1999 |
| JP | 60-243016 | 3/1985 |
| JP | WO 99 34812 | 7/1999 |
| WO | WO 92 13896 | 8/1992 |
| WO | WO 98/11778 * | 3/1998 |

OTHER PUBLICATIONS

Dorland's Medical Dictionary, 25th ed., 1988. pp. 369 and 1043.*

Exon et al., "Effect of Dietary Chlorogenic Acid on Multiple Immune Functions and Formation of Aberrant Crypt Foci in Rats," *J. Toxicology and Environmental Health*, Part A, 53:375–384 (1998).

King et al., "Structure–Activity Relationships: Analogues of the Dicaffeoylquinic and Dicaffeoltartaric Acids as Potent Inhibitors of Human Immunodeficiency Virus Type I Integrase and Replication," *J. Med. Chem.*, 42:497–509 (1999).

Zhu et al., "Irreversible Inhibition of Human Immunodeficiency Virus Type 1 Integrase by Dicaffeoylquinic Acids," *J. Virology*, 73(4):3309–3316 (1999).

* cited by examiner

Primary Examiner—Christopher R. Tate
(74) Attorney, Agent, or Firm—Banner & Witcoff, Ltd.

(57) ABSTRACT

The present invention relates to a preparation for stimulating or enhancing an immune system comprising one or more agents that stimulate T-lymphocytes in vivo. Such a preparation can be sued in the prophylaxis and/or treatment of a medical condition. The invention further relates to a preparation for use in a pharmaceutical or food product and to a preparation for medical use.

29 Claims, No Drawings

CHLOROGENIC ACID AND AN ANALOG THEREOF FOR IMMUNE SYSTEM STIMULATION

The invention relates to a preparation for stimulating the immune system. The invention further relates to a method of treating and/or preventing a medical condition by administration of said preparation to a human or an animal and to a method to manufacture a product for use in prophylaxis and/or treatment of a medical condition.

The immune system in animals, including humans, plays an important role in prevention and treatment of many disorders/diseases, such as infections by foreign bodies such as bacteria, viruses, parasites, toxins or proteins, but also in the prevention and treatment of various forms of cancer. Viruses or bacteria may for example cause infections in the respiratory tract, or cause systemic infections (e.g. herpes virus). Infections may also be associated with other diseases such as an infection by a cytomegalo-virus (CMV) in an AIDS patient or an infection by pneumococcen sp in a cancer patient. Such an infection is also referred to as a secondary infection.

In clinical practice, large groups of hospital patients or other persons suffering from an underdeveloped (e.g. neonates) or compromised (e.g. cancer or transplantation patients treated with chemotherapeutics or part of the elderly population) immune function, suffer at one point in time from (primary or secondary) infections, which may increase the period of hospital stay or the duration of an illness in general. An underdeveloped or compromised immune function of patients may require aggressive treatment with antibiotics, which even can lead to life-threatening situations.

In daily life, also "healthy" persons are frequently infected by a foreign entity such as a virus and/or a bacterium, leading to symptoms such as bad wound healing, pain, fever or general malaise. Commonly known examples thereof are various infections of the respiratory tract, including the throat, and such infections frequently occur in particular after stress (e.g. due to bad weather, heavy exercise or emotional stress).

The functioning of the immune system is inter alia related to various chemical substances that are produced in vivo or obtained by nutrition. Administration of such substances in order to support the immune function can help prevention and/or treatment of many diseases. In addition various substances such as antioxidants, are known to play a beneficial role in the prevention and treatment of diseases. Antioxidants may prevent damage of healthy cells by radicals, formed by the immune system, that are directed against infecting moieties (infectants).

The presence of chlorogenic acid in an antioxidant composition is reported in U.S. Pat. No. 5,788,971. In this publication, sunflower seed extract containing chlorogenic acid and green tea leaf extract containing EGCG is said to be able to scavenge free radicals, which may be useful in the treatment of inflammatory disorders.

European patent application 0/906/761 also mentions chlorogenic as a possible antioxidant.

In JP 60243016 an anti-influenza tablet is described containing 3,5-dicaffeoylqluinic acid obtained by subjecting a methanol extract of a *Helianthus annus* seed to counter-current distribution.

In WO 99/34812 a composition comprising baicalin, chlorogenic acid and forsythiaside is reported to have antiviral, antibacterial or immuno-modulating properties. According to this publication said composition is capable of increasing the natural killer cell (NK cell) activity and the interferon-α production of peripheral blood cell lymphocytes in vitro. It remains unclear from this publication what the contribution of chlorogenic acid is in a composition mentioned in this publication.

With respect to prevention of diseases, there is a limited value to administering substances which may give protection to the subject in a general way. It is however also possible to stimulate the immune system more specifically, such as by vaccination of an animal and human to give protection against a particular disease. Vaccination aims to present an innocuous yet antigenic form of an infectious organism or its toxin(s), for establishing protective immunity. So called T-lymphocytes play an important role in this process. By vaccination the immune system can very specifically be stimulated to become active against a particular antigen. Large vaccination programs, are currently applied, both to animals and to humans, against a wide variety of diseases. This vaccination may cause discomfort to a subject that is vaccinated, and sometimes has limited success.

The present invention seeks to provide a preparation to stimulate or to enhance the immune system of animals or humans to be more effective. Surprisingly it has been found that a preparation comprising one or more agents that stimulate T-lymphocytes proliferation in vivo have the desired effect.

Accordingly the invention relates to a preparation for stimulating or enhancing an immune system comprising one or more agents that stimulate T-lymphocytes in vivo.

Highly suitable agents that stimulate T-lymphocytes in vivo have been found to be chlorogenic acid (1-caffeoylquinic acid) or a functional analog thereof. Preferred examples of chlorogenic acid and functional analogs thereof may be represented by formula 1:

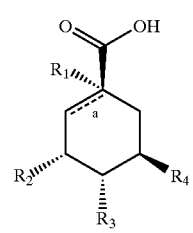

(Formula 1)

wherein "a" represents either a single bond or a double bond and $R_1$ is only present in case "a" represents a single bond, and wherein at least one of the functional groups R1–R4, preferably at least R4, represents a functional group represented by formula 2 (further referred to as subst. II)

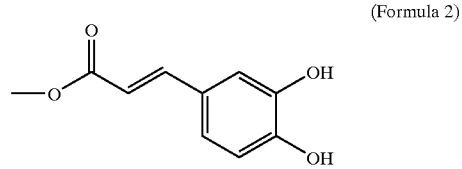

(Formula 2)

and the remaining of said functional groups R1–R4 are independently chosen from the group formed by —OH, and other substituents—like caffeic acid moiety analogs—that are abundant in a material of a vegetable nature and can be split off by the intestinal flora. It is to be noted that the compound of formula 1 has the 1α, 3α, 4α, 5β-hydroxy configuration.

Preferred functional analogs of chlorogenic acid in a preparation according to the invention are 4-caffeoylquinic acid, neochlorogenic acid (3-caffeoylquinic acid), dicaffeoyl quinic acids wherein the 1 and 5 positions are substituted (1,5-dicaffeoylquinic acid), isochlorogenic acids (i.e. dicaffeoyl quinic acids substituted on 3 and 4 positions, 3 and 5 positions or 3, 4 and 5 position (3,4,5 tricaffeoyl quinic acid)), kryptochlorogenic acid (4-O-caffeoylquinic acid, cynarin (1,3-O-caffeoylquinic acid), 1,3,4,5-O-tetracaffeoylquinic acid and caffeoylshikimic acids, in particular 5-O-caffeoylshikimic acid. With reference to formula 1, these analogs have the following chemical structures:

| Compound | $R_1$ | $R_2$ | $R_3$ | $R_4$ |
|---|---|---|---|---|
| (−)-quinic acid | OH | OH | OH | OH |
| 1-O-caffeoyl quinic acid | subst. II | OH | OH | OH |
| chlorogenic acid (5-O-caffeoylquinic acid | OH | OH | OH | subst. II |
| kryptochlorogenic acid | OH | OH | subst. II | OH |
| neochlorogenic acid | OH | subst. II | OH | OH |
| cynarin (1,3-O-dicaffeoylquinic acid) | subst. II | subst. II | OH | OH |
| 1,5-O-dicaffeoylquinic acid | subst. II | OH | OH | subst. II |
| 3,4-O-dicaffeoylquinic acid | OH | subst. II | subst. II | OH |
| 3,5-O-dicaffeoylquinic acid | OH | subst. II | OH | subst. II |
| 4,5-O-dicaffeoylquinic acid | OH | OH | subst. II | subst. II |
| 1,2,3,4-O-tetracaffeoylquinic acid | subst. II | subst. II | subst. II | subst. II |

Chlorogenic acid and functional analogs thereof will be referred to herein as CA-compounds.

A CA-compound in a preparation according to the invention may be of synthetic origin, or of natural origin Chlorogenic acid and derivatives thereof can be synthesized by applying one of the methods known in the art, such as the method described by Panizzi et al. (Gazz.Chim.Ital, 86, 913, (1956)). Alternative sources for chlorogenic acid and its derivatives are inter alia *Vaccinium myrtillus* extracts, potato extracts (pressing juice) and sunflower extracts.

The preparation may comprise plant material in raw form. This may be advantageous, in particular to lower the cost-price of preparation. A CA-compound in the preparation is preferably of natural origin, e.g. as an extract of one or more plants. The extracts (or raw material) can for example be taken from plants like Echinacea sp., green coffee bean, green cacao bean, hawthorn, green tea, elder tree, artichoke (*Cynara scolymus*), guerana, butterbur. Pheonix spp, *Butia capitata,* Dandelion, various members of the dicotylus plants, in particular members of the Compositae, as well as *Arnica montana* and Birch tree or combinations thereof. Several suitable extraction methods are known in the art. A highly preferred extraction method typically comprises crushing of the plant material, blending the crushed material with a polar, preferably aqueous, solvent, filtering the slurry of crushed material and polar solvent and purifying the filtrate. Several purification methods like one-sep or multi-step liquid-liquid extraction, solid-phase extraction, chromatography and the like are known from the state of the art. A possible extraction method is disclosed in WO 99/34812.

The T-lymphocyte stimulating properties of CA-compounds may give an important boost to the activity of the immune systems. The term "T-lymphocytes" is commonly used to describe a family of leucocytes originating from lymphoid progenitors that have differentiated in the thymus and descended cells thereof. Cytotoxic lymphocytes may develop from precursors which are activated by antigen plus major histocompatibility complex class I (MHC class I) and are expanded and mature by the action of interleukin-2 and ill-defined maturation factors produced by helper T-lymphocytes. [ref Ivan Roitt, Essential Immunology, $7^{th}$ Ed., (1991) Blackwell Scientific Publications, Oxford, UK]. T-lymphocytes have several crucial functions in the immune system. They are responsible for the recognition of an entity which is foreign to the body (an antigen) and they are involved in the development of a specific immune response in order to eliminate an antigen. Such an antigen may be a pathogen originating from outside the body, like a bacterium, a virus or parasite, but it may also be a neoplastic somatic cell that has obtained a neo-antigenic structure. A protein or peptide structure such as a prion, a vaccine or a toxin as well as other non-cell structures can also be antigenic. Once an antigen has entered the body, it is taken up, processed and presented by so called antigen presenting cells, i.e. dendritic cells, to precursor T-lymphocytes. Subsequently, those T-lymphocytes that recognize the antigen need to proliferate in order to mount a significant immune response. Activated (helper) T-lymphocytes are required to support the formation of specific antibodies by B-lymphocytes, which predominantly clear foreign entities from the body.

In addition the helper T-lymphocytes (T-helper cells) support the formation of cytotoxic T-lymphocytes, which are inter ala able to eliminate virus-infected cells or neoplastic cells which are developed in several forms of cancer. Cytotoxic T-lymphocytes may also play a role in the defense against a parasite and they are able to release interferon-gamma. Interferon-gamma may contribute to making cells surrounding an infected cell resistant to viral spread.

In order to be effective it is crucial that the specific T-helper cells are abundant in sufficient numbers or proliferate to reach sufficient numbers, as soon as possible after the appearance or arising of an antigen in the body. It has been found that a preparation according to the invention can be used to increase the proliferation of antigen-specific T-lymphocytes, such as T-helper cells and cytotoxic T-lymphocytes. A preparation may also promote differentiation of cells to become functional T-lymphocytes.

A preparation according to the present invention may also stimulate T-helper cells to develop particular cytokines which support other types of lymphocytes. Examples of such lymphocyte supporting cytokines are interleukin-2 (IL-2), interleukin-6 (IL-6) and interferon-gamma (IFN-γ).

The general nature of the immune stimulating properties of preparations according to the invention enables it employment in a broad field of applications. The person skilled in the art will recognize that the type of foreign entity is not essential. Some examples of viruses against which a preparation according to the invention stimulates the immune system are DNA viruses, like Pox-viridae, Herpes-viridae (e.g. herpes, simplex, varicella zoster virus, CMV), Adenoviridae, Papavoviridae, Hepadnaviridae, Parvoviridae, RNA viruses like Reo-viridae, Picorna-viridae (e.g. Polio-virus, Echo-virus, Entero-virus, Rhino-virus), Toga-virdae, Flavi-viridae, Corona-viridae, Rhabdo-viridae, Paramyxo-viridae (e.g. parainfluenza, Mumps, measles and RS virus), Orthomixo-viridae, Filo-viridae, Bunya-viridae, Arena-viridae, Calici-viridae, and Retroviridae. According to the invention also Papilloma, influenza, HIV, HTLV, Corona and Eppstein Barr can be prevented or treated.

Bacterial infections that can be prevented or treated by using a preparation according to the invention include those that can occur as a secondary infection after a virus infection (for example after a common cold) or during another disease. The preparation can be used to stimulate lymfocytes against all kinds of bacteria. Some examples are pneumococcus sp, *Staphylococcus aureus* and bacteria that enter the blood circulation e.g in situations of gut leakage, sepsis and the like.

Some examples of parasites against which the invention can be directed are protozoan and metazoan parasites, including but not limited to *Leishmania donovani, Trypanosoma cruzi, Toxoplasma gondii*, Plasmodium sp., *Theilaria parva* and Schistosomas sp.

As already indicated, a preparation according to the invention stimulates or induces T-lymphocytes in a general way. It has been found that the preparation is particularly suitable for use before, during and after situations in which the immune system is highly challenged in order to increase the resistance of a patient or a "healthy" person. Such situations may be surgery, heavy physical exercise, exposure to bad weather conditions, sore throat, coughing, fever, general malaise and the like.

The present preparation is however not only effective in the prophylaxis and/or treatment of infection by one or more antigens, but the immune system may also be stimulated to deal with a neoplastic cell which may develop in several forms of cancer. Thus the invention can help to decrease tumor growth, optionally in combination with prevention or treatment of occasional infections that may occur during or after cancer therapy, such as radiation- or chemotherapy. Accordingly the invention relates to a preparation for stimulating T-lymphocytes for use in treatment and/or prophylaxis of cancer, infection by a parasite, a toxin, a virus, and/or a bacterium, to a method for stimulating T-lymphocytes by administration of said preparation and to a method which is part of a prophylactic or treatment protocol for cancer. Such a protocol includes, but is not limited to, a vaccination protocol with autologous tumor cells, tumor antigen autologous dendritic cells or other immunotherapeutic protocols used in the treatment of different cancers. In addition to a general stimulation of T-lymphocytes, it has surprisingly been found that in an embodiment of the invention, further comprising an innocuous yet antigenic form of an infectious organism and/or a toxin thereof, chlorogenic acid and/or a functional analog thereof may also act as an adjuvant, i.e. chlorogenic acid and/or a functional analog thereof may stimulate the specific immune response, directed by T-lymphocytes, against said infectious organism and/or said toxin. Besides a more general effect that a CA-compound may have on the immune system, as an adjuvant, a CA-compound may enable an antigen to be presented more effectively to a T-lymphocyte, or even to be transported into a T-lymphocyte and possibly to activate that particular T-lymphocyte. Thus the CA-compound may enable or enhance the induction of an immune response against the particular pathogenic antigen, against which the vaccine is directed. Thus T-lymphocyte stimulation by a CA-compound allows the use of a preparation according the present invention to be used in a vaccine. Accordingly, an embodiment of the invention is a vaccine comprising chlorogenic acid and/or a functional analog thereof as adjuvant.

The use of a chlorogenic acid or a functional analog thereof as adjuvant is another embodiment of the invention. It may be used in a vaccine for immunization of a subject or a population. The vaccine may further comprise one or more additives, such as those that will be discussed below. The method of vaccination may be orally or subcutaneously or by another method known in the art. In a preferred embodiment the vaccine is administered orally.

For various reasons, a preparation according to the invention may comprise a one or more other active substances or additives. It has been found that a stimulation of T-lymphocytes can further be enhanced if a preparation according to the invention further comprises a particular type of cytokine or an agent that is capable of inducing such type of cytokine. The presence of such a compound may lead to a quicker and/or larger immune response, which may be particularly desirable when fast recovery of a patient is wanted e.g. due to his bad condition, or for economical reasons. A larger response is also useful in case one aims to prevent the use of antibiotics, e.g. because development of tolerance of a micro-organism against an antibiotic is feared.

The additional effect of a cytokine inducing agent in combination with a CA-compound also allows inclusion of lower amounts of said CA-compound in a preparation without decrease in effectiveness. This reduction can lead to a reduced cost-price and improved organoleptic properties of preparations according to the invention.

Interferon-gamma is a preferred cytokine in relation to this invention and accordingly a cytokine inducing agent in a preparation should preferably be capable of inducing the production of interferon-gamma. It is to be noted that preparations intended for oral administration will generally not contain interferon-gamma itself, but rather an agent capable of inducing the production of interferon-gamma, as it may be digested in the gastro-intestinal tract. In preparations for other types of administration, such as vaccines, interferon-gamma itself may be used. Preferred examples of interferon-gamma inducing agents are specific polysaccharides, zinc salts and N-acetyl cysteine. Suitable zinc sources can for example be any edible food-grade zinc salt, such as an inorganic salt like zinc carbonate, zinc sulfate, zinc oxide, zinc chloride etc. Examples of suitable polysaccharides are arabinogalactans from *Baptisa tinctoria*, Echinacea species, *Larix occidentalis, Angelica acutiloba* or other polysaccharides that can be isolated from Echinacea species, *Thuja occidentalis* and *Panax ginseng*. Polysaccharides from fungi, in particular from *Flammulina velupites* may also be used.

Polysaccharides that can enhance the cellular immune response are thought to induce interferon production as well, e.g. polysaccharides from *Arnica montana* cell cultures (stimulating TNFα release in macrophages), Plantago spp (increasing NK cell activity), *Achyrocline satureioides, Aconitum officinalis, Angelica acutiloba, Aristolochia officinalis, Astralagus gummerifa, A. membranaceus, A. mongholicus, Avena sativa, Bambusa vulgaris, Baptisia tinctoria, Bryonia dioica, Calendula officinalis, Carthamus tinctorius, Chamomilla recutita, Echinacea angustifolia, E. pallida, E. purpurea, Eleutherococcus senticosus, Eupatorium cannabinum, Silene vulgaris, Thuja occidentalis, Triticum sativum, Vincetoxicum officinalis, Viscum album.*

Naturally a preparation according to the invention may also comprise several cytokine inducing agents, including the ones mentioned above.

A preparation according to the invention for use in the treatment of cancer may also comprise one or more compounds with an anti-tumor activity. Examples of such compounds include polysaccharides which demonstrate anti-tumor activity in vivo. These are thought to act via a similar pathway as the polysaccharides stimulating interferon production such as mentioned above. In general they also have an immunostimulating activity. Examples are polysaccharides (in particular β-1,3-glucans and/or β-1,4-glucans) from the mushrooms, *Lentinus edodes* (lentinan), *Schizophyllum commune* (schizophyllan), *Phytophtora parasytica, Grifola frondosa, Sclerotinia clerotiorum, Ganoderma lucidum, Coriolus versicolor* (krestin) and the like, or from the plants *Morinda citrifolia* fruit or *Viscum album* and the like.

The anti-carcinogenic effect of β-1,3-glucans is shown in U.S. Pat. No. 4,454,286, for example for β-1,3-glucans from *Schizophyllum commune*, Auricularia spp and lentinan from

*Lentinus edodes*. Methods for isolating polysaccharides such as arabinogalactans from a larch tree are disclosed in U.S. Pat. Nos. 2,073,616 and 4,950,751.

U.S. Pat. No. 5,096,708 shows the induction of T-helper cells by thuja polysaccharides and the antiviral effect against retroviruses in vitro.

A preferred preparation according to the present invention, comprises chlorogenic acid and/or a functional analog thereof and N-acetylcystein, for medical use. Surprisingly such a preparation shows a particularly well synergistic effect in medical use. Not only is NAC capable of inducing interferon-gamma, but it is also a scavenger of hydrogen peroxide and may inhibit activation of NF-κB and (rhinovirus mediated) IL-8 release. Furthermore NAC may enhance the glutathion status, which may be important for providing protection against oxygen radical related damage. Preferably the weight to weight ratio of chlorogenic acid and/or a functional analog thereof (CA-compound) to N-acetylcystein (NAC) is about 0.005-4 CA-compound/NAC, more preferably 0.02–1 CA-compound/NAC and most preferably 0.045–0.5 CA-compound/NAC.

In a preferred embodiment the preparation further comprises one or more additional ingredients, such as anti-inflammatory agents, antioxidants, trace elements, minerals, vitamins, extracts of plants and the like.

Under specific conditions, as for example can occur in patients that suffer from chronically inflamed tissues, it may be advantageous to include certain anti-inflammatory components in the composition. Preferred anti-inflammatory agents areacetylsalicylic acid, apocynin, curcumin and equivalents thereof as well as mixtures of these components. As an equivalent of acetylsalicylic acid can be considered salicylic acid or salts thereof as well as extracts of plants that are sources of these compounds, such as Salix spp Functional equivalents of apocynin are considered to be related acetophenones and glycosides thereof, such as those that can be found in Picrorhiza species. Curcumin can be applied as pure synthetic component, as a functional analog—such as tetrahydroxy-curcumin—or as an extract from a plant that is rich in Curcuma species.

Effective amounts of these anti-inflammatory compounds are known in the art and are usually in the range of 5–4000 mg, and preferably 50–1000 mg per daily dose of acetylsalicylic acid, aponycin or curcumin or analogs thereof.

A preparation according to the present invention preferably comprises one or more other antioxidants, other than a CA-compound or NAC. Ascorbic acid and α-tocopherol are particularly preferred examples of suitable antioxidants in the preparation. Other suitable antioxidants are for example flavenoids, catechins, proanthocyanidins or other polyphenols.

In a preferred embodiment the preparation comprises one or more trace elements, such as manganese, copper or selenium. A trace element may be added in a solution or a crystalline form, e.g. of a medical grade trace element oxide, -carbonate, -citrate, gluconate and the like. A trace element may also be added to the preparation in the form of a natural product, rich or enriched in trace elements, e.g. a yeast or a plant extract. Trace elements may have various functions. Several trace elements, including manganese, copper and selenium, are vital elements of various enzymes. Enzymes like superoxide dismutases (e.g. those that are copper-dependent) and gluthathion peroxidase (selenium dependent) can act as antioxidants. Furthermore trace element supplements may be administered in a case of a potential deficiency of a trace element in a patient e.g. as a symptom of a disease or as the result of the administration of a particular (pharmaceutical) compound, such as NAC, of which it is known that it may lead to an increase of urinary zinc excretion.

A preferred preparation comprises an extract of one or more plants, such as plant extracts from Echinacea, e.g. *Echinacea purpurea, Astragalus membranaceus, Panax ginseng*, artichoke and the like. These extracts may be alcoholic and/or aqueous extracts. Echinacea extract is preferably obtained from the dried pressed juice of the fresh "subterranean" parts of the plant, or alternatively by an aqueous-ethanolic extract of the roots, standardized to alkylamides; Ginseng may be prepared according to any method and is preferably standardized to ginsenosides or polysaccharides; Artichoke may be prepared according to any method and is preferably standardized to caffeoyl acid derivatives.

The extracts may be dried, or mixed in a liquid and may provide various active compounds, such as polysaccharides which have been found capable of inducing release of interferons or have another function.

Particularly good results have been achieved with preparations comprising one or more compounds selected from the group formed by ginsenosides, beta glucans, e.g. β-1,3-D-glucan, lipoic acids and L-carnitine and analogs thereof.

A lipoic acid, preferably alfa-lipoic acid (thioctic acid) can be included as pure synthetic compound, such as a racemate of the oxidized form. It could however also be in the form of the pure biologically active isomer in reduced form. Analogs are considered to be salts thereof as well as the lipoic acid amide. The compound is preferably administered in an amount of 1–100 mg per daily dose.

L-carnitine may be present as a synthetic compound or as acylated compound. The daily consumption of carnitine it typically in the range of 0.01–2 grams.

β-glucans can be isolated from plants (e.g. barley) or micro-organisms (Sacccharomyces sp). Isolation methods are known in the art (e.g. EP 0 606 080 and WO 92-13896). The daily dose of β-glucans is preferably 0.2–10 grams A preparation may also comprise additives such as flavors, coloring agents, aroma's, preservatives and the like. A variety of examples of such additives are known from the art.

A preparation according to the invention can be widely used for a variety reasons and to a variety of subjects of any age and of various species including humans. The concentration of a substance present in a preparation according to the invention may vary widely based upon several factors. These factors include the species to be treated (e.g. cattle, a pet or a human), the condition of the subject to be treated, the reason for administration (e.g. a particular diagnosis or prophylaxis), or the form of a preparation (e.g. a concentrated tablet, dissolved in a drink or mixed in cattle- or pet feed). In a preferred embodiment a preparation comprises one or more substances shown in Table 1, more preferably in a daily dose as indicated in Table 1. Herein "daily dose" is used to describe a daily dose for a primate having a body weight 70 kg, unless stated otherwise. Methods to calculate the daily dose for other subjects will be known to the skilled professional. Once the daily dose is determined it can be calculated how much of a certain preparation needs to be administered, knowing the (approximate) fraction of active components and additives in the preparation.

TABLE 1

Preferred daily dose (based upon a preparation for a primate) of some substances in a preparation for stimulating T-lymphocytes in vivo.

| Substance | preferred relative concentration (daily dose in mg) |
|---|---|
| Chlorogenic acid and/or functional analogs thereof (CA-compounds) | 0.5–500 |
| N-acetylcystein | 50–2000 |
| Zinc (ionic) | 1–200 |
| Beta glucans | 2–200 |
| Echinacea extract (e.g. *Echinacea premium*) | 200–2000 |
| Ginsenosides (e.g. as extract from Panax Ginseng) | 0.2–150 |
| Ascorbic acid | 10–1000 |
| α-tocopherol | 1–1000 |
| Copper (ionic) | 0.1–20 |
| Selenium (ionic) | 0.005–0.3 |
| lipoic acid | 1–100 |
| L-carnitine | 10–2000 |
| *Astragalus membranaceus* extract (dry material) | 200–20000 |

In a much preferred embodiment, the preparation comprises 2–300 mg/day, and a most preferably 10–200 mg/day, of one or more CA-compounds and 50–2000 mg/day N-acetylcystein, plus optionally one or more of the other compounds in an amount as can be deducted from Table 1. Most preferably N-acetylcystein is present in a daily dose of 100–1000 mg.

Particularly preferred are also preparations comprising one or more CA-compounds, zinc and/or one or more polysaccharides in a concentration in the range shown in Table 1.

In another preferred embodiment a preparation comprises a mixture of 4-caffeoylquinic acid, 5-caffeoylquinic acid and 1,5-dicaffeoylquinic acid in a dose of 2–300 mg. A preferred distribution of CA-compounds in such a dose is 25–40 mole % 4-caffeoylquinic acid, 25–40 mole % 5-caffeoylquinic acid and 25–40 mole % 1,5-dicaffeoylquinic acid. In a more preferred preparation the distribution of CA-compounds is 30–35 mole %. for each of these three compounds.

When present, substances mentioned in Table 1, are preferably present in a preparation to match the daily recommended dose as indicated in Table 1.

It is further an advantage of the invention that the CA-compounds and other components comprised by the preparation are often natural products, which have substantially no negative side effects upon administration. This makes it possible to market the preparation as an over the counter drug, which means that it can be sold without prescription of a physician. Moreover it has surprisingly been found that it is possible to process preparations according to the invention in food&drinks products, which may further facilitate the accessibility of products of the invention to the public, which more an more becomes aware of the importance of health-food products as an aid to maintain one's general health. The invention also provides in a novel food&drink product, by its capability to stimulate the immune system, and in particular T-lymphocytes.

For the manufacture of a product for stimulating T-lymphocytes in vivo, a preparation according to the invention may be used. The preparation may be processed by methods known from the pharmaceutical and food&drinks processing industries into a pharmaceutical, a drink or a food product.

In a preferred embodiment the preparation may be in a more or less solid form such as a capsule, a tablet, a lozenge, a powder, an agglomerate, a snack, a bar or a paste. The preparation may also be a solution, a liquid or a semi-liquid shaped product, such as a gel, an emulsion, a suspension, a drink (such as a lemonade, a fruit juice, a dairy drink) a pudding, an ice cream, a sauce and the like.

A preparation may be processed in a drink or food product at the factory. A drink, comprising a daily dose may for example be packed in a 250 ml package, or another volume that is suitably consumed by a subject. In another embodiment the active components are present in a bar of typically up to 25 g, which may further comprise typically at least 60% of (sweet) carbohydrates. In another embodiment, a preparation, e.g. a powder, a liquid, a suspension and the like, may be administered to a drink or food, such as a dessert or a juice, relatively shortly before oral intake. Such a preparation may for example substantially consist of active components and may in principle by administered by anyone.

The preparation may also be a complete food product, e.g. for patients on a particular (strict) diet or for cancer patients.

In a preferred method for stimulating T-lymphocytes, a preparation according to the invention is administered to a patient, in the form of a capsule, a tablet, a powder or a lozenge. In another embodiment the preparation may be administered in another form such as drops or a potion.

For the formulation of the dosage form, the above described preparation may suitably be combined with a pharmaceutically acceptable (carrier. A much preferred dosage form is the tablet, in which the preparation may be combined with usual tablet constituents such as filler-binders, lubricants and the like.

The dosage in which the preparation is to be administered will of course depend on the concentration of active ingredients of the preparation and on the severity of the medical disorder or disease that is to be treated or prevented. The person skilled in the art will be able to optimize and formulate a suitable dosage scheme based on his ordinary knowledge of the field.

Preferably the preparation is orally administered, although other administration methods known in the art may also be applied, for some embodiments.

The packaging preferably occurs to facilitate convenience of packaging, storage, transport and/or consumption, and to ensure stability of the product, using methods known in the art.

The invention will now be further elucidated by the following, non-restrictive examples.

EXAMPLE 1

Tablet for stimulating T-lymphocytes in vivo

Main Purpose: for use in prevention and/or treatment of common cold and influenza Daily Dose: 2 tablets

TABLE 2 active compounds in a tablet

| Substance | Amount | Extra information |
|---|---|---|
| Ascorbic Acid (95%) | 125 mg | |
| Sodium selenate[1] (selenium yeast 0.2%) | 85 μg | (providing 35 μg Selenium) |
| Zinc citrate[2] | 22 mg | (providing 7.5 mg Zinc |
| Cupric Gluconate[3] | 7.5 mg | (providing 1 mg Copper) |
| N-acetylcysteine (99%) | 200 mg | |

TABLE 2-continued active compounds in a tablet

| Substance | Amount | Extra information |
|---|---|---|
| Dried pressed *Echinacea purpura* juice (Flachsman) | 200 mg | (no significant amount of chlorogenic acid reported) |
| Dried extract of artichoke (globe artichoke extract 5% chlorogenic acid) | 180 mg | (providing 9 mg chlorogenic acid) |
| Dried extract of Panax ginseng (14% ginsenosides) | 50 mg | (providing 7 mg ginsenosides) |
| Dried (1:4) extract of *Astragalus membranaceus* (crude drug extract ratio; Nutratech) | 250 mg | (no significant amount of chlorogenic acid reported) |

[1]Alternatively also other form of selenium, such as sodium selenite or selenomethionine or a combination thereof may be used. Sodium may be replaced by another counter ion, such as potassium.
[2]Alternatively also zinc oxide (about 80% Zn), zinc carbonate (about 52% Zn), other zinc salts or a combination thereof may be used.
[3]Alternatively also cupric oxide (about 80% Cu) and/or other copper salts may be used.
[1,2,3]Also yeast that is enriched with these trace elements may be used.
tablet was made by mixing and pressing as known in the art.

EXAMPLE 2

Powder for stimulating T-lymphocytes in vivo; for use in drink or dessert

Main Purpose: for use in treatment common cold

Daily Dose: powder from one sachet

TABLE 3 active compounds in one sachet with powder

| Substance | Amount | Extra information |
|---|---|---|
| Ascorbic Acid | 250 mg | |
| Sodium selenate | 170 µg | (providing 70 µg Selenium) |
| Zinc citrate | 45 mg | (providing 15 mg Zinc |
| Cupric Gluconate | 15 mg | (providing 2 mg Copper) |
| N-acetylcysteine | 100 mg | |
| β 1,3 D glucans | 8 mg | |
| Dried pressed *Echinacea purpura* juice | 900 mg | |
| Chlorogenic acid | 18 mg | |
| Dried extract of Panax ginseng | 120 mg[1] | (providing 17 mg ginsenosides) |
| Maltodextrins | 5 g | |
| Flavor | 100 mg | |

[1]In an alternative preparation 200 mg dried extract of Panax ginseng was used.

EXAMPLE 3

Tablet for stimulating T-lymphocytes in vivo

Main Purpose: prevention and/or treatment of common cold and influenza

TABLE 4 active compounds in a tablet

| Substance | Amount |
|---|---|
| Ascorbic Acid | 60 mg |
| α-Tocopherol | 20 mg |
| Sodium selenite | 80 µg |
| Zinc oxide | 22 mg |
| N-acetylcysteine | 200 mg |
| Chlorogenic acid | 30 mg |

Tablets were made by the same method as in Example 1.

EXAMPLE 4

A preparation was made according to Table 3, but Chlorogenic acid was replaced by an mixture of 20 mg 4-caffeoyl quinic acid, 20 mg 5-caffeoylquinic acid and 30 mg 1,5-dicaffeoylquinic acid.

EXAMPLE 5

Preparations according to examples 1–3 were made wherein the Echinacea (Flachsman) extract was replaced by a mixture of pupurea root ethanol/water extract (53%) and *E. angustifolia* root ethanol/water extract (47%) standardized to approximately 2% alkylamides (Mediherb). Furthermore *Panax ginseng* was replaced by *Panax quinquefolium* aqueous extract containing mainly oligosaccharides and polysaccharides (CV Technologies).

What is claimed is:

1. A preparation for stimulating or enhancing an immune system having one or more agents that stimulate T-lymphocytes in vivo comprising 10–200 mg chlorogenic acid and/or one or more functional analogs thereof and 50–2000 mg N-acetylcysteine.

2. A preparation according to claim 1, wherein said functional analog is selected from the group consisting of chlorogenic acid, 4-caffeoylquinic acid, 5-caffeoylquinic acid, 1,5-dicaffeoylquinic acid, isochlorogenic acid, 3,4,5 tricaffeoyl quinic acid, 1-O-caffeoylquinic acid, 1,3-O-caffeoylquinic acid, 1,3,4,5-O-tetracaffeoylquinic acid, and 5-O-caffeoylshikimic acid.

3. A preparation according to claim 1, wherein said functional analog is a compound represented by formula 1 and functional analogs thereof,

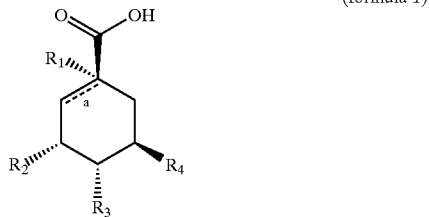

(formula 1)

wherein "a" represents either a single bond or a double bond, and $R_1$ is only present when "a" represents a single bond, and wherein at least one of the functional groups $R_1$–$R_4$ represents a functional group represented by formula 2 and functional analogs thereof

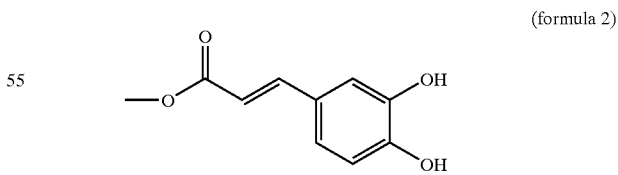

(formula 2)

and the remaining of said functional groups $R_1$–$R_4$ are —OH or a functional group represented by formula 2 or functional analogs thereof.

4. A preparation according to claim 1, further comprising one or more interferon-gamma inducing agents selected from the group consisting of polysaccharides, zinc, and/or *Astragalus membranaceus* extract.

5. A preparation according to claim 1 for use in treatment of cancer, a toxin, or infection by a parasite, a virus, and/or a bacterium.

6. A preparation according to claim 1 for use in increasing the resistance of an individual to cancer, a toxin, or infection by a parasite, a virus, and/or a bacterium.

7. A preparation according to claim 1, further comprising Echinacea species extract, an antioxidant, a trace element, a mineral, an anti-tumor agent, a ginsenoside, lipoic acid, and/or L-carnitine.

8. A preparation according to claim 4, wherein the polysaccharide is an arabinogalactan.

9. A preparation according to claim 7, wherein the anti-tumor agent is a beta glucan.

10. A preparation according to claim 7, wherein the mineral is zinc.

11. A preparation according to claim 7, wherein the trace element is chosen from the group consisting of manganese ions, copper ions, selenium ions, and selenium compounds.

12. A preparation according to claim 7, wherein the Echinacea species is selected from the group consisting of *Echinacea premium, Echinacea angustifolia, Echinacea pallida,* and *Echinacea purpurea.*

13. A preparation according to claim 1, further comprising an antioxidant chosen from the group consisting of ascorbic acid and α-tocopherol.

14. A preparation for stimulating or enhancing an immune system having one or more agents that stimulate T-lymphocytes in vivo comprising: 10–200 mg chlorogenic acid and/or functional analogs thereof, 50–2000 mg N-acetylcysteine, 200–2000 mg Echinacea species extract, 0.2–150 mg ginsenosides, 2–200 mg beta glucans, 10–1000 mg ascorbic acid, 1–1000 mg α-tocopherol, 1–200 mg zinc, 0.1–20 mg copper, 0.005–0.3 mg selenium, 1–100 mg lipoic acid, 10–2000 mg L-carnitine, and *Astragalus membranaceus* extract of 200–20,000 mg dry material.

15. A preparation according to claim 14, wherein said functional analog is selected from the group consisting of chlorogenic acid, 4-caffeoylquinic acid, 5-caffeoylquinic acid, 1,5-dicaffeoylquinic acid, isochlorogenic acid, 3,4,5 tricaffeoyl quinic acid, 1-O-caffeoylquinic acid, 1,3-O-caffeoylquinic acid, 1,3,4,5-O-tetracaffeoylquinic acid, and 5-O-caffeoylshikimic acid.

16. A preparation according to claim 14, wherein said functional analog is a compound represented by formula 1 and functional analogs thereof,

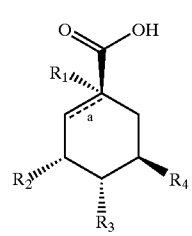

(formula 1)

wherein "a" represents either a single bond or a double bond, and $R_1$ is only present when "a" represents a single bond, and wherein at least one of the functional groups $R_1$–$R_4$ represents a functional group represented by formula 2 and functional analogs thereof,

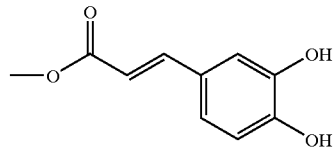

(formula 2)

and the remaining of said functional groups $R_1$–$R_4$ are —OH or a functional group represented by formula 2 or functional analogs thereof.

17. A preparation according to claim 14, wherein said chlorogenic acid and/or a functional analog thereof originates from one or more plants.

18. A preparation according to claim 17, wherein the functional analog is derived from extracts from one or more plants selected from the group consisting of Echinacea sp., green coffee bean, green cacao bean, hawthorn, green tea, elder tree, artichoke, guerana, butterbur, Phoenix spp, *Butia capitata,* Dandelion, a dicotylus Compositae or other dicotylus, *Arnica montana,* and Birch tree.

19. A preparation according to claim 14, further comprising one or more arabinogalactans selected from the group consisting of *Baptisa tinctoria,* Echinacea species, *Larix occidentalis, Angelica acutiloba* and/or other polysaccharides from Echinacea species, *Thuja occidentalis, Panax ginseng, Flammulina velupites, Arnica montana,* Plantago spp, *Achyrocline satureioides, Aconitum officinalis, Angelica acutiloba, Aristolochia officinalis, Astralagus gummerifa, A. membranaceus, A. mongholicus, Avena sativa, Bambusa vulgaris, Baptisia tinctoria, Bryonia dioica, Calendula officinalis, Carthamus tinctorius, Chamomilla recutita, Echinacea angustiolia, E. pallida, E. purpurea, Eleutherococcus senticosus, Eupatorium cannabinum, Silene vulgaris, Triticum sativum, Vincetoxicum officinalis,* and *Viscum album.*

20. A preparation according to claim 14, further comprising manganese ions and/or selenium compounds.

21. A preparation according to claim 14, wherein the preparation is in the form of a pharmaceutical, drink, or food product.

22. A preparation according to claim 14 in a daily dosage form.

23. A preparation according to claim 21, wherein the pharmaceutical, drink, or food product is selected from the group consisting of a capsule, a tablet, a lozenge, a powder, an agglomerate, a paste, a solution, a liquid, a gel, an emulsion, a suspension, a bar, a drink, a pudding, an ice cream, and a sauce.

24. A preparation according to claim 14 for use in treatment of cancer, a toxin, or infection by a parasite, a virus, and/or a bacterium.

25. A preparation according to claim 24 for use in treatment of an infection by an infectant selected from a member of the group consisting of Poxviridae, Herpesviridae, Adenoviridae, Papovaviridae, Hepadnaviridae, Parvoviridae, Reoviridae, Picornaviridae, Togaviridae, Flaviviridae, Coronaviridae, Rhabdoviridae, Paramyxoviridae, Orthomyxoviridae, Filoviridae, Bunyaviridae, Arenaviridae, Calciviridae, Retroviridae, Papillomaviridae, influenza virus, HIV, HTLV, corona virus, Epstein Barr virus, pneumococcus, and *Staphylococcus aureus.*

26. A preparation according to claim 14 for use in increasing the resistance of an individual to cancer, a toxin, or infection by a parasite, a virus, and/or a bacterium.

27. A preparation according to claim 26 for use in increasing the resistance of an individual to infection by an infectant selected from a member of the group consisting of Poxviridae, Herpesviridae, Adenoviridae, Papovaviridae, Hepadnaviridae, Parvoviridae, Reoviridae, Picornaviridae, Togaviridae, Flaviviridae, Coronaviridae, Rhabdoviridae, Paramyxoviridae, Orthomyxoviridae, Filoviridae, Bunyaviridae, Arenaviridae, Calciviridae, Retroviridae, Papillomaviridae, influenza virus, HIV, HTLV, corona virus, Epstein Barr virus, pneumococcus, and *Staphylococcus aureus*.

28. A preparation according to claim 14 wherein the Echinacea species is selected from the group consisting of *Echinacea premium, Echinacea angustifolia, Echinacea pallida,* and *Echinacea purpurea*.

29. A preparation according to claim 14, further comprising arabinogalactan.

* * * * *